United States Patent [19]

Cue, Jr. et al.

[11] 4,431,828

[45] Feb. 14, 1984

[54] REGENERATION OF 6-FLUORO-4-CHROMANONE FROM BY-PRODUCTS IN THE SYNTHESIS OF SORBINIL

[75] Inventors: Berkeley W. Cue, Jr., Gales Ferry; Philip D. Hammen, East Lyme; Stephen S. Massett, Groton, all of Conn.

[73] Assignee: Pfizer Inc., New York, N.Y.

[21] Appl. No.: 440,657

[22] Filed: Nov. 10, 1982

[51] Int. Cl.³ ........................................... C07D 311/22
[52] U.S. Cl. .................................... 549/401; 549/404; 548/309
[58] Field of Search ............................... 549/401, 404

[56] References Cited

U.S. PATENT DOCUMENTS 4,130,714 12/1978 Sarges ................................. 548/309
4,286,098 8/1981 Sarges ................................. 548/309

*Primary Examiner*—Nicky Chan
*Attorney, Agent, or Firm*—Charles J. Knuth; Albert E. Frost; Robert K. Blackwood

[57] ABSTRACT

6-Fluoro-4-chromanone, a sorbinil intermediate, is regenerated from enantiomeric and mixtures of enantiomeric and racemic compounds obtained as major by-products in the synthesis of sorbinil. The regenerated intermediate is useful in the synthesis of additional sorbinil.

14 Claims, No Drawings

REGENERATION OF 6-FLUORO-4-CHROMANONE FROM BY-PRODUCTS IN THE SYNTHESIS OF SORBINIL

BACKGROUND OF THE INVENTION

The synthesis of sorbinil, by optical resolution of RS-2,3-dihydrospiro[4H-1-benzopyran-4,4'-imidazolidine]-2',5'-dione (the racemic compound corresponding to sorbinil) or of precursor 6-fluoro-4-ureidochroman-4-carboxylic acid affords at least equal yields of the undesired enantiomer of sorbinil or of its precursor (either one usually contaminated with the corresponding racemate). The overall efficiency of the process is greatly enhanced by conversion of these by-products back to sorbinil intermediate, 6-fluoro-4-chromanone, which is then recycled to sorbinil. Not only is the overall yield of sorbinil greatly increased, but disposal problems associated with these by-products (necessarily formed in yields at least equivalent to sorbinil or its precursor) are avoided.

The present invention is applicable not only in the original synthesis of sorbinil, involving optical resolution of racemate with brucine (Sarges, U.S. Pat. No. 4,130,714), but also to more recently discovered processes: Sysko, U.S. patent application Ser. No. 440,686 for "Sorbinil by Optical Resolution with Aminopinane Derivatives"; and Cue and Moore, U.S. patent application Ser. No. 440,641, by "Sorbinil for Optical Resolution of Precursor 6-Fluoro-4-Ureidochroman-4-Carboxylic Acid"; both filed concurrently with the present application).

SUMMARY OF THE INVENTION

Flowsheet I incorporates synthetic routes to sorbinil according to Sarges, Sysko and Cue et al. (supra), as well as the present reconversion of by-products to 6-fluoro-4-chromanone.

The present invention encompasses a process for the regeneration of purified 6-fluoro-4-chromaone (1) from by-product R- or a mixture of R- and RS-6-fluorospiro[chroman-4,4'-imidazolidine]-2',5'-dione [(7) or (7) and (3)], or a mixture of R- and RS-6-fluoro-4-ureidochroman-4-carboxylic acid [(8) or (8) and (4)], or a cationic salt thereof, which comprises the steps of:

(a) hydrolysis in the presence of an aqueous inorganic base to form an intermediate amino acid which is R- or a mixture of R- and RS-4-amino-6-fluorochroman-4-carboxylic acid (2);

(b) degradation of said intermediate amino acid in an aqueous solvent with a chlorinating agent to form a mixture of 6-fluoro-4-chromanone and 6-fluoro-4-chloriminochroman [the mixture (9)]; and (c) hyrogenation of said mixture of 6-fluoro-4-chromanone and 6-fluoro-2-chloroiminochroman over a noble metal catalyst in an aqueous or aqueous organic solvent to yield said purified 6-fluoro-4-chromanone (1), suitable for recycling to additional sorbinol.

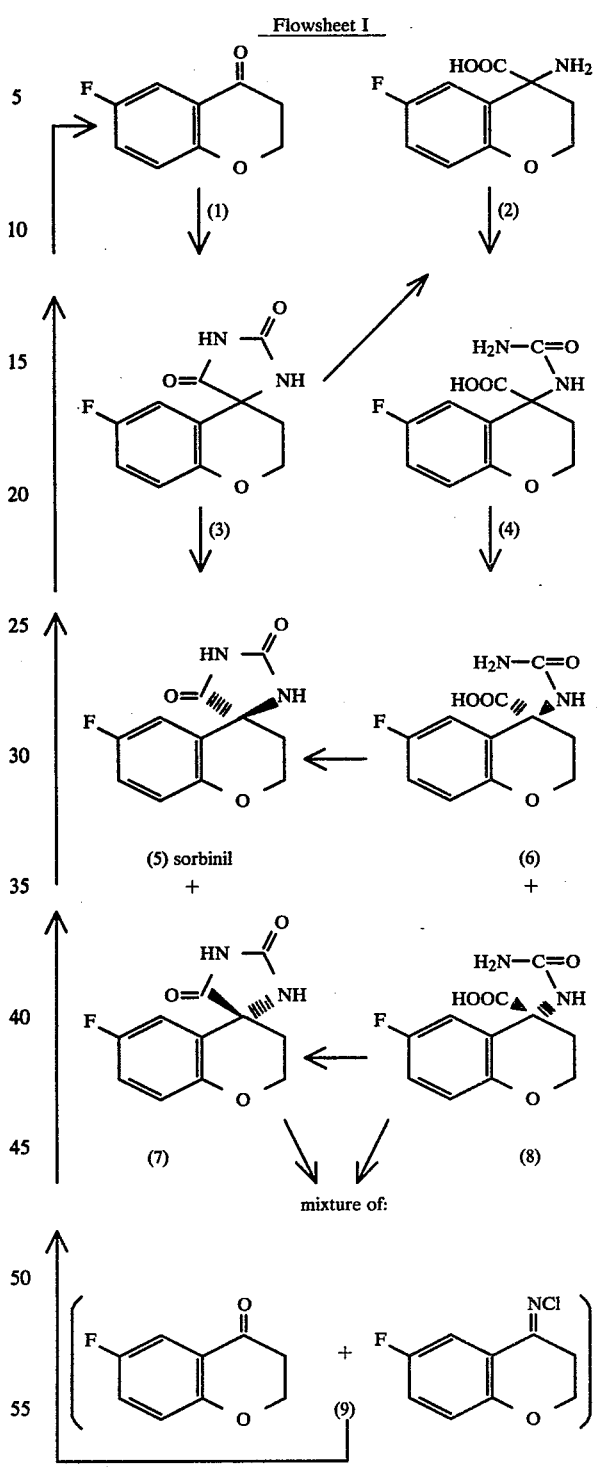

Flowsheet I mixture of:

The expression "cationic salt" includes, but is not restricted to, alkali metal salts (e.g. sodium, potassium), alkaline earth salts (e.g. calcium, magnesium) and salts with amines (e.g. ammonia). In a preferred embodiment, the salt will be with an optically active amine which was used in the resolution of the racemate (3) or (4). When regeneration of 6-fluoro-4-chromanone is from (7) or a mixture of (7) and (3), the most preferred salts are with brucine (used by Sarges, supra) or (−)-3-aminomethylpinane, (+)-3-aminomethylpinane, (−)-2- amino-2-norpinane or quinine (all used by Sysko, supra). Of the latter, most highly preferred is (—)-3-aminomethylpinane, since in that case only one optically active amine is employed, facilitating recovery of the amine. When regeneration of 6-fluoro-4-chromanone is from (8) or a mixture of (8) and (4), most preferred salts are with D-(+)-(1-phenethyl)amine or L-(—)-ephedrine (used by Cue et al., supra).

When the salt is that of an optically active amine, a further preferred embodiment of the present invention is to recover the optically active amine in step (a) above, by extraction of the basic aqueous reaction mixture with a water immiscible, reaction inert organic solvent. The amine is recovered from the extract by standard methods of evaporation, precipitation and/or distillation. As used herein, the expression "reaction inert solvent" refers to a solvent which will not interact with starting materials, reagents, intermediates or product so as to significantly reduce the yield or purity of the desired product-in the present instance the optically active amine and, ultimately, the 6-fluoro-4-chromanone, both to be used in recycling to produce additional sorbinil.

The expression "chlorinating agent" refers to any chlorinating agent commonly employed in the art, including, but not restricted to chlorine, N-chlorolower alkanoic acid amides (e.g. N-chloroacetamide), hydrocarbon dicarboxylic acid imides (e.g., N-chlorosuccinimide, phthalimide and the like), N-loweralkanoyl anilides; 3-chloro and 3,5-dichloro-5,5-dimethylhydantoin, perchloride hydrohalides (e.g., pyridinium perchloride hydrochloride), and lower alkyl hypochlorites (e.g., tert-butylhypochlorite). Preferred reagents are N-chlorosuccinimide or sodium hypochlorite (equivalent to Cl$_2$+NaOH). When N-chlorosuccinimide is employed as chlorinating agent, it is preferred to adjust the pH from step (a) and maintain it at 4–5.5 during the degradation step (b). When sodium hypochlorite is used as chlorinating agent, it is preferred not to adjust the pH down from step (a), avoiding release of chlorine gas from the system in the degradation step (b).

DETAILED DESCRIPTION OF THE INVENTION

The present invention, which is readily carried out, makes otherwise undesired and unavoidable by-products in the synthesis of sorbinil of value in the preparation of additional sorbinil.

When sorbinil is obtained by optical resolution of racemic (RS)-6-fluorospiro[chroman-4,4'-imidazolidine]-2',5'-dione (3), i.e. as the enantiomeric salt with an optically active amine (e.g. brucine, (—)-3-aminomethylpinane, supra), the enantiomer of sorbinil, i.e., R-6-fluorospiro[chroman-4,4'-imidazolidine]-2',5'-dione (7), is obtained in a yield at least equivalent to that of sorbinil. The by-product R-isomer will generally be initially recovered as the diasteromeric salt (which usually contains also some of the sorbinil salt). The recovered diastereomeric salt can be used directly in the process of the present invention, preferably with in process recovery of the optically active amine. Alternatively, the enantiomeric salt is converted, e.g. by simple slurry in excess aqueous mineral acid or by elution from a suitable basic ion exchange resin followed by contact with acid, into its free acid form (7), usually containing also some racemate (3); the free acid form is then used in the process of the present invention.

When sorbinil is obtained by the optical resolution of racemic (RS-) 6-fluoro-4-ureidochroman-4-carboxylic acid, the R-isomer thereof is obtained in a yield at least equivalent to that of the S-isomer (sorbinil precursor). Again, the by-product is generally initially recovered as the diastereomeric salt (which usually contains some of the S-isomer salt). The latter R-isomer or mixture is (i) used directly in the present process, preferably with in process recovery of the optically active amine; (ii) converted by simple slurry in mineral acid, or contact with basic ion exchange resin followed by contact with acid, to the free acid form (8), usually contaminated with racemate (4), then used in the present process; or (iii) converted to the hydantoin (7), i.e. the enantiomer of sorbinil, usually containing racemate (3), then used in the present process.

The first stage of the present process is hydrolysis of the hydantoin (7), the hydantoin mixture (7) and (3), the ureidoacid (8) or the ureidoacid mixture (8) and (4), or a cationic salt thereof, to R-4-amino-6-fluorochroman-4-carboxylic acid, or a mixture of that R-amino acid and the racemic amino acid (2). This hydrolysis is carried out in the presence of an aqueous inorganic base (e.g., an alkali or alkaline earth hydroxide such as NaOH or Ba(OH)$_2$). When the hydantoin is the starting material, Ba(OH)$_2$ is the preferred base. When the ureidoacid is the starting material, NaOH is the preferred reagent. In either case, the hydrolysis is carried out by warming to 75°–130° C. (under pressure, if necessary). Most convenient is the reflux temperature of the reaction mixture, which will generally be in the range of 100°–110° C., depending upon the molar concentration of solutes.

If desired, the amino acid can be recovered, e.g. by adjusting the pH to the isoelectric point (near neutral) and filtration or extraction into a water immiscible organic solvent. It is preferred, however, to use the amino acid without isolation in the subsequent chlorination step.

If the starting material introduced into the basic hydrolysis step is a salt of an optically active amine, the amine is generally recovered during the hydrolysis stage by extraction into a water immiscible organic solvent such as methylene chloride, chloroform, toluene or ethyl acetate, preferably at 25°–50° C., i.e. before or after heating at 75°–130° C., most preferably before the heating period so as to minimize side reactions involving the optically active amine.

The second stage of the present process involves chlorination of the intermediate amino acid with overall conversion to a mixture (a) of 6-fluoro-2-chromanone and 6-fluoro-2-chloroiminochroman. The second stage is generally carried out directly on the aqueous amino acid derived in the first stage, with optional pH control in the second stage. In any event, even if carried out on isolated amino acid, the second stage, like the first stage, is carried out in aqueous media. Temperature is not critical, e.g., 0°–50° C. is satisfactory. As a matter of convenience, ambient temperatures (e.g., 17°–27° C.) are preferred. The mixed product is simply isolated from the aqueous reaction mixture by filtration, preferably at high pH (8.5–10.5).

The proportion of ketone and chlorimine in the mixture formed in the second stage will depend upon the clorinating agent and the conditions of the chlorination. Under one set of preferred conditions, viz., N-chlorosuccinimide as chlorinating agent with pH controlled between 4 and 5.5, the ketone will predominate, particularly when the amino acid is not isolated and is a mixture derived from the hydantoin with barium hydroxide as base. On the other hand, under a second preferred set of conditions, using sodium hypochlorite as the chlorinating agent (without pH adjustment), the chlorimine will predominate, particularly when the amino acid is not isolated and is a mixture derived from ureidoacid in strong aqueous sodium hydroxide.

The third stage of the present process is the hydrogenation of the ketone/chlorimine mixture (9), carried out under hydrolytic (aqueous) conditions, usually with an added reaction-inert water miscible organic solvent to help solubilize at least a portion of the mixture (9). Methanol is the preferred solvent for this purpose, generally added not only prior to hydrogenation, but after hydrogenation to help separate the purified product from insoluble catalyst.

The hydrogenation is carried out over a hydrogenation catalyst, preferably a noble metal catalyst such as platinum, palladium, rhenium, rhodium and ruthenium, either of the supported or non-supported type, including the known catalytic compounds thereof such as the oxides, chlorides, etc. Examples of suitable catalysts supports include carbon, silica and barium sulfate. The catalysts may be preformed or formed in situ by prereduction of an appropriate salt of the catalytic compound. Examples of preferred catalysts are 5% palladium-on-carbon, 5% platinum-on-carbon, 5% rhodium-on-carbon, platinum chloride, palladium chloride, platinum oxide and ruthenium oxide. Palladium, particularly palladium on carbon, is the most highly preferred catalyst for the present process, since complete conversion of the chlorimino compound is readily achieved under mild conditions. Temperature is not a critical variable in the hydrogenation, temperatures in the range of 0°–100° C. being generally satisfactory. As a matter of convenience, ambient temperature (17°–27° C.) is preferred, since at this temperature hydrogenation occurs at a reasonable rate with a reasonable level of catalyst, and costs associated with heating or cooling are avoided. ressure is likewise not critical, with pressures ranging from subatmospheric to 100 atmospheres or more being satisfactory. Since the required equipment is much less elaborate and expensive, moderate pressures (2–8 atmospheres) are preferred.

The 6-fluoro-4-chromanone recovered by the process of the present invention is suitable for reconversion to racemic hydantoin (3) by the method of Sarges (supra), or further to racemic ureidoacid (4) by the method of Cue et al. (supra); resolution of (3) or (4) according to Sarges, Sysko or Cue et al. (supra); and recovery of enantiomeric by-products for further recycling. The methods of Sarges are found in the above cited U.S. Pat. No. 4,130,714. The methods of Sysko and Cue et al. are included in the specific examples provided below.

The present invention is illustrated by the following examples. However, it should be understood that the invention is not limited to the specific details of these examples. All temperatures are in °C. Where not specified, temperatures are ambient. Where not specified, solvent stripping is in vacuo.

EXAMPLE 1

Sorbinil via Its (−)-3-Aminomethylpinane Salt (−)-3-Aminomethylpinane HCl, 9.5 g (46.6 mmole), ethyl acetate (186 ml) and 1 N NaOH (93 ml) were stirred vigorously for 10 minutes. The organic layer was separated, washed 1×93 ml H$_2$O, dried (MgSO$_4$) and stripped to yield (−)-3-aminomethylpinane free base as an oil, 7.75 g (99%) [alpha]$_D^{25}$= −54.85° (c=1 in methanol), which was then dissolved in 20 ml methanol.

Racemic 6-fluorospiro[4H-1-benzopyran-4,4'-imidazolidine]-2',5'-dione (10.0 g, 42.3 mmoles) was dissolved in 214 ml 2-propanol and 194 ml methanol, heated to reflux, and the above solution of amine added, providing a clear solution at the 71° reflux temperature. The solution was slowly cooled (crystallization began at 27°) and stirred at room temperature for 6 hours. The crude (−)-3-aminomethylpinane salt of sorbinil was recovered by filtration and dried in vacuo at 40°, 6.81 g, mp 127.5°–196° (dec.), [alpha]$_D^{25}$= −8.2° (c=1 in methanol). Step yield: 79.6%. The mother liquor therefrom is evaporated to dryness to yield crude (−)-3-aminomethylpinane salt of the enantiomer of sorbinil, the main contaminant being (−)-3-aminomethylpinane of sorbinil.

Crude sorbinil salt (6.7 g) was dissolved at reflux in 80.4 ml of 1:1 methanol:isopropanol, cooled slowly to room temperature, and the resulting solids granulated 2 hours. Purified salt recovered by filtration with 4 ml 1:1 methanol:isopropanol wash, and dried in vacuo at 40° C., 4.42 g, m.p. 119°–208° (dec.), [alpha]$_D^{25}$= +3.9° (c=1 in methanol). Step yield: 66%.

Purified salt (4.33 g, 10.7 mmole) was distributed into 107.5 ml ethyl acetate and 53.8 ml 1 N HCl. The organic layer was separated, washed 1×54 ml 1 N HCl, 1×54 ml H$_2$O and 1×54 ml brine, dried (MgSO$_4$), filtered, evaporated in vacuo to a slurry, chased 3×50 ml ethyl acetate to a final volume of 12 ml, granulated 3 hours, filtered and dried in vacuo at 40° to yield sorbinil, 2.18 g, mp 234°–242°, [alpha]$_D^{25}$= +51.2° (c=1, methanol). Step yield: 86.2%. Alternatively, the dried organic layer is extracted with an equivalent of 1 N NaOH. The extract is separated and freeze dried to yield the sodium salt of sorbinil.

The above aqueous layers from sorbinil recovery were combined (226 ml), combined with 113 ml CH$_2$Cl$_2$ and the pH adjusted to 10.0 with 25% NaOH. The aqueous layer was separated and extracted with 55 ml fresh CH$_2$Cl$_2$. The CH$_2$Cl$_2$ layers were combined, evaporated in vacuo to 60 ml, washed 1×30 ml H$_2$O, dried (MgSO$_4$) and evaporated to yield recovered (−)-3-aminomethylpinane; oil, 1.58 g, [alpha]$_D^{25}$= −55.5° (c=1, methanol).

Sorbinil was further purified by dissolving in 20 ml hot ethanol, concentrated to ½ volume and granulating 4 hours at room temperature. Purified sorbinil was recovered by filtration and dried at 40° in vacuo, 1.82 g, mp 234°–241.5°, [alpha]$_D^{25}$= +53.1. Step yield: 91%. Overall yield: 41.2%.

By the same extraction techniques as those described above, the above crude (−)-3-aminomethyl-pinane salt of the enantiomer of sorbinil is converted to (−)-3-aminomethylpinane, suitable for recycle, and to the enantiomer of sorbinil, contaminated with racemate.

EXAMPLE 2

Crude 6-Fluoro-4-Chromanone from Sorbinil Enantiomer and Racemate

Levorotatory (R-) and/or racemic (RS-) 6-fluorospiro-[chroman-4,4'-imidazolidine]-2',5'-dione (100 g, 0.423 mmole) was slurried in 750 ml H$_2$O. Ba(OH)$_2$.8-H$_2$O (267.0 g, 0.846 mole) was added and the resulting thin slurry refluxed 48 hours. The resulting heavy suspension was cooled to 60°–65° and NH$_4$CO$_3$ (100 g, 0.876 mole) added. The slurry was then stirred 30 minutes and filtered at 50°–55° with 300 ml of warm water wash of the collected inorganic salts. The combined filtrate and wash was adjusted from pH 8.5 to 4.5–5.0 with hydrochloric acid. To the acidified solution, N-chlorosuccinimide (57.0 g, 0.427 mole) was added portionwise over 5 hours at 30–45 minute intervals. The resulting slurry was stirred 17 hours at room temperature, then 1 hour at 15°. Solids were recovered by filtration, taken up in $CH_2Cl_2$, treated with activated carbon, and $CH_2Cl_2$ displaced with hexane to a pot temperature of 68°–69° and a final volume of 400–500 ml, during which crystallization occurred. After cooling and digestion for 1 hour at 20°–25°, purified title product was recovered by filtration, 50.2 g, having the physical properties of the known material.

Title product prepared in this manner contains 6-fluoro-4-chloriminochroman as an impurity. The latter interferes with further use of title product in the synthesis of additional sorbinil. Said impurity is removed (being converted to the desired 6-fluoro-2-chromanone) according to the following Example.

EXAMPLE 3

Purification of Crude 6-Fluoro-4-chromanone by Hydrogenation

Crude 6-fluoro-4-chromanone, containing 6-fluoro-4-chloriminochroman as an impurity (5.0 g), 5% Pd/C (50% water wet, 0.25 g), and 1:1 $H_2O:C_2H_5OH$ (100 ml) were combined and the mixture hydrogenated at 45 psig of hydrogen (4 atmospheres) for 2 hours, by which time tlc on silica gel (using toluene:methyl ethyl ketone:acetic acid 5:2:1 as eluant) indicated absence of faster moving chlorimine ($R_f$ 0.8) in the 6-fluoro-2-chromanone ($R_f$ 0.7). The reaction mixture was diluted with 100 ml of methanol (to completely dissolve solids other than catalyst), the catalyst recovered by vacuum filtration on a pad of diatomaceous earth, and the filtrate evaporated in vacuo to 50 ml (from a water bath at 45°), cooled to 5°, granulated for 15 minutes and filtered to yield purified title product, 2.65 g, mp 108°–112°, tlc as indicated above.

EXAMPLE 4

RS-4-Amino-6-fluorochroman-4-carboxylic Acid

A stirred slurry of RS-6-fluorospiro[chroman-4,4'-imidazolidine]-2',5'-dione, (78 g, 0.33 mole) and Ba-$(OH)_2.8H_3O$ (208.3 g, 0.66 mole) in 585 ml $H_2O$ was slowly heated to reflux over 3 hours and refluxed 16 hours. The slurry was cooled to 80° and powdered $NH_4CO_3$ (78 g) added portionwise over 5 minutes. Moderate foaming was noted. After stirring 1.5 hours at 80°, the mixture was cooled to 60° and filtered over diatomaceous earth with $2\times100$ ml hot $H_2O$ for wash. The combined filtrate and washes were stripped to 200 ml and allowed to stand overnight. 2-Propanol (600 ml) was added and the mixture heated to 70° to dissolve precipitated solids. The hot solution was treated with activated carbon, filtered over diatomaceous earth and washed with hot 1:1 $H_2O$:2-propanol. The combined filtrate and washes were stripped to 200 ml, and water chased with $3\times300$ ml fresh 2-propanol. The resulting thick slurry was diluted with 200 ml additional 2-propanol, cooled to 5°, granulated 0.5 hour, filtered and air dried to yield title product, 63.6 g, 91.2%, mp 252–253 (dec.).

EXAMPLE 5

RS-6-Fluoro-4-ureidochroman-4-carboxylic Acid

Method A

Title product of the preceding Example (21.1 g, 0.1 mole) was slurried in 250 ml $H_2O$. KOCN (16.2 g, 0.2 mole) was added portionwise over 2.5 minutes. The almost complete solution was stirred 22 hours at 23°, during which the pH increased from 6.8 to 9.1 and complete solution occurred. Concentrated HCl (19.0 ml) was added over 1 hour, keeping temperature 25°–29° C. The resulting slurry was granulated 1 hour (pH 3.2–3.5), and title product recovered by filtration with 150 ml $H_2O$ wash, partially dried in air and then for 18 hours at 50°–55° in vacuo, 20.0 g, 79%.

Method B

The same starting imidazolidine used in the preceding Example (47.2 g, 0.2 mole) and NaOH pellets (28 g, 0.7 mole) were combined in 600 ml $H_2O$ and heated at reflux for 40 hours. The reaction mixture was cooled to 24° and the pH lowered from 11.8 to 5.0 with 6 N HCl. Gassing was noted below pH 8. After stirring the slurry for 20 minutes at pH 5, KOCN (32.5 g, 0.4 mole) was added over 2 minutes, the mixture stirred 20 hours and a small amount of solids removed by filtration with 50 ml water for wash. The combined filtrate and wash was adjusted from pH 8.5 to 4.0 with 6 N HCl. Precipitated title product was recovered by filtration, washed with warm water and air dried, 39.7 g (78%), mp 198–199 (dec.).

Alternatively the NaOH hydrolysis stage was carried out at 118° and 27 psig for 18 hours. Further reaction with KOCN and isolation as immediately above likewise gave title product, 38.8 g (76.4%), mp 199–200 (dec.).

Alternatively KOH (26.4 g, 85%, 0.4 mole) was substituted for NaOH, with a reflux time of 22 hours. Reaction with KOCN and isolation as immediately above likewise gave title product, 36.8 g (72.4%), mp 198–199 (dec.).

EXAMPLE 6

D-(+)-(1-Phenethyl)ammonium S-6-Fluoro-4-ureidochroman-4-carboxylate

Title product of the preceding Example (10.0 g, 39.4 mmole) was slurried in 400 ml of methanol at $45\pm5°$ for 1 hour. Over 4 minutes 4.87 g (40.1 mmole) of D-(+)-(1-phenethyl)amine in 45 ml methanol was added to the resulting thin slurry, yielding a solution. The bath was removed, the mixture cooled slowly to ambient temperature, the mixture granulated for 16 hours, and crude title product recovered by filtration and dried at 60° in air, 6.4 g, 86.6%, mp 206°–210°, $[alpha]_D^{25} = +54.3°$ (c=0.3, methanol). Crude title product, 6 g, was repulped in 180 ml methanol at 40°–50° for 1 hour, cooled to ambient temperature, granulated 3 hours, filtered and air dried to yield purified title product, 4.4 g, mp 214°–216°, $[alpha]_D^{25} = +69°$ (c=0.3 in methanol), 73.3% recovery, overall 63.5% yield.

The mother liquor from crude title product was stripped to yield a mixture consisting primarily of D-(+)-(1-phenethyl)ammonium R-6-fluoro-4-ureidochroman-4-carboxylate togeher with title product, 8.3 g, mp 198°–200° C., $[alpha]_D^{25} = -35.4°$ (c=0.5, methanol], suitable for recycle to 6-fluoro-4-chromanone.

Under one option, this salt mixture is distributed between ethyl acetate and water, with the pH first adjusted to 10. The ethyl acetate layer is separated and optically active amine recovered by evaporation. The pH of the aqueous phase is then adjusted to 1-2 with hydrochloric acid and extracted with fresh ethyl acetate. The organic phase is washed with additional small portions of water, dried (MgSO$_4$) and evaporated to yield a mixture of R and RS-6-fluoro-4-ureidochroman-4-carboxylic acid.

EXAMPLE 7

Sorbinil

Title product of the preceding Example (4.3 g, 11 mmoles) was slurried in 30 ml glacial CH$_3$CO$_2$H at 93° C. for 2 hours, a solution resulting after the initial 15 minutes. The mixture was cooled to 60° and stripped to 10 ml. Warm water (21.5 ml, 50°) was added, resulting in a slurry having pH 3.5. After 5 minutes, the pH was adjusted to 4.5 with 4 ml 4 N NaOH (temperature now 28°) and the mixture cooled to 20° over 30 minutes. Filtration gave relatively pure sorbinil directly, 2.35 g, 90.3%, mp 238°-241° C., $[alpha]_D^{25} = +52.7°$ (c=1, methanol). Sorbinil was purified by dissolving 2.2 g in 27.4 ml boiling acetone, clarified by hot filtration and the mother liquor stripped to 13 ml. The resulting slurry was twice slowly diluted with 17.2 ml of hexane and stripped to 13 ml. Filtration and air drying gave purified sorbinil, 1.924 g, 87.5%, mp 239.5°-242.5°, $[alpha]_D^{25} = +54.5$ (c=1, methanol).

Relatively pure sorbinil, 56.2 g, mp 237°-241°, $[alpha]_D^{25} = +52.3°$ (c=1, methanol), prepared in like manner in 89.8% yield from title product of the preceding Example was dissolved in 700 ml of boiling acetone, clarified by filtration and stripped to 300 ml. Hexane (400 ml) was slowly added and the mixture restripped to 300 ml. Hexane addition and stripping was repeated, yielding purified title product, vacuum dried at 40° C. for 18 hours, 54.9 g, 97.7%, mp 236°-241°, $[alpha]_D^{25} = +53.4°$ (c=1 in methanol).

EXAMPLE 8

L-(−)Ephedrine Salt of S-6-fluoro-4-ureidochroman-4-carboxylate Acid

Method A

Title product of Example 2 (35.6 g, 0.14 mole) was slurried 1.07 liters acetone, stirred at reflux (59°) for 30 minutes, and cooled to 54°. L-(−)-ephedrine (24.4 g, 0.148 mole) was added in one portion. The slurry thinned and near solution resulted. After less than 2 minutes at 55° rapid crystallization began. The slurry was refluxed 2 hours, cooled to 40° C. and sugar-like crystals of crude title product recovered by filtration, 26.1 g; mp 204° (dec.); $[alpha]_D^{25} = +37.0$ (c=1, methanol).

Mother liquor at ambient temperature gave a second crop of solids, 1.3 g, mp 180°-185° (dec.); $[alpha]_n^{25} = 0$ (c=1, methanol).

Concentration of mother liquor gave foamy solids, 32.9 g, mp 72°-90° (dec.); $[alpha]_D^{25} = -55.7°$ (c=1, methanol).

First crop solids (25 g) was repulped in 250 ml of refluxing acetone, recovered after cooling to 40°, 24 g; mp 205° (dec.); $[alpha]_D^{25} = +38.2$ (c=1, methanol). Evaporation of mother liquor to dryness gave 1.2 g, mp 90°-110° (dec.); $[alpha]_D^{25} = +31.4°$ (c=1, methanol).

Once repulped solids (13 g) were repulped in 260 ml of refluxing acetone, recovered after cooling to 45°, 11.7 g, $[alpha]_D^{25} = +39.3$ (c=1, methanol). Evaporation of mother liquor gave an additional 1.1 g of solids.

Method B

Title product of Example 2 (100 g) was stirred at reflux (65°) in 374 ml methanol for 30 minutes, then cooled to 59°. Water (7.42 ml) and L-(−)-ephedrine (68 g) were added, resulting in heavy precipitation. The slurry was refluxed at 66° for 45 minutes, cooled to 27° and highly purified title product directly recovered by filtration, 70.4 g, $[alpha]_D^{25} = +44.36$ (c=1.04 in methanol). The filtrate was evaporated to yield the crude diastereomeric salt, L-(−)-ephedrine R-6-fluoro-4-ureidochroman-4-carboxylate, 116.3 g.

EXAMPLE 9

R- and RS-6-Fluoro-4-ureido-Chroman-4-carboxylic Acid

Method A

Recovered D-(+)-(1-phenethyl)ammonium R-6-fluoro-4-ureidochroman-4-carboxylate (containing also in minor portion the corresponding D-ammonium S-carboxylate salt), 32.3 g, was combined with 215 ml of 1 N HCl and stirred at 16°-23° for 21 hours. Title product was recovered by filtration, 20.6 g, 94%, mp 195°-198° (dec.).

Method B

A column containing a 50 ml volume of previously used ion exchange resin (Amberlite IRA 900) was slowly flushed sequentially with 250 ml deionized H$_2$O, 250 ml 1 N NaOH, 250 ml N$_2$ sparged H$_2$O and 250 ml N$_2$ sparged methanol. Crude enantiomeric salt (10 g) in 50 ml methanol was placed on the column and eluted with an additional 100 ml of methanol and evaporated in vacuo to yield recovered ephedrine, 0.0199 mole, by titrimetric assay with 0.1 N HCl in methanol. The column was then eluted with 150 ml of methanol containing 4.4 g dry HCl and finally with 150 ml of fresh methanol. The latter methanol HCl and methanol eluants were combined and evaporated in vacuo to yield enantiomeric (R) and racemic (RS) 6-fluoro-4-ureidochroman-4-carboxylic acid, 5.86 g.

EXAMPLE 10

Crude 6-Fluoro-4-chromanone from R- and RS-6-Fluoro-4-ureidochroman-4-carboxylic Acid Title product of the preceding Example (100 g) was slurried in 475 ml H$_2$O. 50% NaOH, 32 g, was added; producing incomplete solution. The mixture was warmed over 40 minutes to a pot temperature of 100° (reflux), by which time there was complete dissolution. Reflux was continued 18 hours and the mixture cooled. The pH was 9.6 and tlc indicated incomplete reaction. The pH was increased to 12.0 with 13.8 g of 50% NaOH and the mixture reheated to reflux for 2.5 hours, at which time tlc on silica gel (toluene:methyl ethyl ketone:acetic acid 5:2:1 as eluant) indicated no more than traces of starting material ($R_f$ 0.5) with high level of intermediate R- and RS-6-fluoro-4-aminochroman-4-carboxylic acid ($R_f$ 0.0). The reaction mixture was cooled to 20° and, maintaining temperature less than 30°, adjusted to pH 4.5 with concentrated HCl, as a precipitate formed. N-chlorosuccinimide (53 g) was added over 15 minutes, maintaining temperature less than 30° C. and the pH 4.0–4.5 by the simultaneous addition of 7 ml of 50% NaOH. The reaction mixture was stirred 1 hour at 25° C., by which time the pH was 5.2 and tlc (above system) indicated complete conversion of intermediate amino acid to products. The pH was then adjusted to 9.6 with about 27 ml of 50% NaOH, the basic slurry granulated for 2 hour at 20°, and title product recovered by filtration, 50.0 g, mp 55°–58° (partial) 65°–75° (complete, but melt not clear); tlc (above system) indicated title product ($R_f$ 0.7) containing 6-fluoro-4-chloroiminochroman ($R_f$ 0.8).

Alternatively, D-(+)-(1-phenethyl)ammonium R-6-fluoro-4-ureidochroman-4-carboxylate, containing in minor portion the corresponding D-ammmonium S-carboxylate is used in the present process. In the initial stage of the process, the salt is distributed between the 50% NaOH and an equal volume of $CH_2Cl_2$. The aqueous phase is washed 2× with one third volume of $CH_2Cl_2$. The organic layers are combined and stripped to yield D-(+)-(1-phenethyl)amine suitable for recycling. The aqueous phase is carried through the balance of the present process to yield title product.

EXAMPLE 11

6-Fluoro-4-Chloriminochroman from R- and RS-6-fluoro-4-ureidochroman

The preceding Example was repeated on one tenth scale to obtain intermediate R- and RS-6-fluoro-4-aminochroman-4-carboxylic acid in NaOH solution. To the solution was added (dropwise) 15% w/w NaOCl (48.2 ml), maintaining temperature 20°–30°. The mixture was stirred 3.5 hours at 20°–25°, by which time tlc (system as in preceding Example) indicated conversion of amino acid to essentially clean title product, with light trace of 6-fluoro-4-chromanone. Title product was recovered by filtration, 3.8 g, $R_f$ 0.8 in above system.

EXAMPLE 12

6-Fluoro-4-chromane from Chlorimine

Title product of the preceding Example (3.6 g) and 5% Pd/C, 50% water wet (0.18 g dry basis) were combined in 72 ml of methanol:water 9:1. The pH was adjusted to 2.0 with concentrated HCl and the mixture hydrogenated at 40–45 psig (3.7–4 atmospheres) of hydrogen for 2 hours. Catalyst was recovered by filtration on a pad of diatomaceous earth. The filtrate showed only title product by tlc ($R_f$ 0.7 in system of immediately preceding Examples), readily recovered by evaporation in vacuo. Tlc indicated some product was retained on the catalyst cake, readily recovered by repulp of the catalyst cake in methanol.

We claim:

1. A process for the regeneration of purified 6-fluoro-4-chromanone from R- or a mixture of R- and RS-6-fluorospiro[chroman-4,4'-imidazolidine]-2',5'-dione, R- or a mixture of R- and RS-6-fluoro-4-ureidochroman-4-carboxylic acid, or a cationic salt thereof, which comprises the steps of:
    (a) hydrolysis in the presence of an aqueous inorganic base to form an intermediate amino acid which is R- or a mixture of R- and RS-4-amino-6-fluorochroman-4-carboxylic acid;
    (b) degradation of said intermediate amino acid in an aqueous solvent with a chlorinating agent to form a mixture of 6-fluoro-4-chromanone and 6-fluoro-4-chloriminochroman; and
    (c) hydrogenation of said mixture of 6-fluoro-4-chromanone and 6-fluoro-4-chloroiminochroman over a noble metal catalyst in an aqueous or aqueous organic solvent to yield said purified 6-fluoro-4-chromanone.

2. A process of claim 1 wherein the purified 6-fluoro-4-chromanone is regenerated from R- or a mixture of R- and RS-6-fluorospiro[chroman-4,4'-imidazolidine]-2',5'-dione, or a cationic salt thereof.

3. A process of claim 2 wherein the cationic salt is an optically active amine salt which in the hydrolysis step (a) further comprises recovery of said optically active amine by extraction into a water immiscible organic solvent.

4. A process of claim 2 wherein the purified 6-fluoro-4-chromanone is regenerated from R- or a mixture of R- and RS-6-fluoro[chroman-4,4'-imidazolidine]-2',5'-dione.

5. A process of claim 4 wherein the chlorinating agent in step (b) is N-chlorosuccinimide or NaOCl.

6. The process of claim 5 wherein the chlorinated agent is N-chlorosuccinimide and the pH is adjusted from step (a) and maintained at 4–5.5 during the degradation step (b).

7. A process of claim 1 wherein the purified 6-fluoro-4-chromanone is regenerated from R- or a mixture of R- and RS-6-fluoro-4-ureidochroman-4-carboxylic acid, or a cationic salt thereof.

8. A process of claim 7 wherein the cationic salt is an optically active amine salt which in the hydrolysis step (a) further comprises recovery of said optically active amine by extraction into a water immiscible organic solvent.

9. A process of claim 8 wherein the optically active amine is D-(+)-(1-phenethyl)amine or L-(−)ephedrine, and the chlorinating agent in step (b) is N-chlorosuccinimide or NaOCl.

10. The process of claim 9 wherein the optically active amine is D-(+)-(1-penethyl)amine, the chlorinating agent is N-chlorosuccinimide, and the pH is adjusted from step (a) and maintained at 4–5.5 during the degradation step (b).

11. A process of claim 7 wherein the purified 6-fluoro-2-chromanone is regenerated from R- or a mixture of R- and RS-6-fluoro-4-ureidochroman-4-carboxylic acid.

12. A process of claim 11 wherein the chlorinating agent in step (b) is N-chlorosuccinimide or NaOCl.

13. The process of claim 12 wherein the chlorinating agent is N-chlorosuccinimide and the pH is adjusted from step (a) and maintained at 4–5.5 during the degradation step (a).

14. The process of claim 12 wherein the chlorinating agent in step (b) is NaOCl, without pH adjustment from step (a).

* * * * *